US006936733B2

United States Patent
Cazaux et al.

(10) Patent No.: US 6,936,733 B2
(45) Date of Patent: Aug. 30, 2005

(54) METHOD FOR PREPARING DISODIUM 2,2'-DITHIOBIS(ETHANESULPHONATE)

(75) Inventors: Jean-Bernard Cazaux, Aramon (FR); Eric Manginot, Montfavet (FR); Marc Veyrat, Le Pontet (FR)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 70 days.

(21) Appl. No.: 10/333,422
(22) PCT Filed: Jul. 17, 2001
(86) PCT No.: PCT/FR01/02312
§ 371 (c)(1),
(2), (4) Date: Jun. 16, 2003
(87) PCT Pub. No.: WO02/06216
PCT Pub. Date: Jan. 24, 2002

(65) Prior Publication Data
US 2004/0024246 A1 Feb. 5, 2004

(30) Foreign Application Priority Data
Jul. 18, 2000 (FR) .............................. 00 09386

(51) Int. Cl.[7] ..................... C07C 319/24; C07C 319/02; C07C 323/66
(52) U.S. Cl. .................................... 562/103
(58) Field of Search ................ 562/103, 30, 101

(56) References Cited

U.S. PATENT DOCUMENTS

| 5,808,140 A | * | 9/1998 | Haridas | 562/8 |
| 5,922,902 A | * | 7/1999 | Haridas | 562/20 |
| 6,504,049 B1 | * | 1/2003 | Kochat | 562/103 |

FOREIGN PATENT DOCUMENTS

| WO | 98/14426 | * | 4/1998 | ......... C07C/319/04 |

OTHER PUBLICATIONS

Database CAPLUS on STN, Doc. No. 110:7669, (XP–002160848) CS 252564 (Sep. 17, 1987) (abstract).*
Database CAPLUS on STN, Doc. No. 87:52754, BE 842665 (Dec. 8, 1976) (abstract).*

* cited by examiner

Primary Examiner—Brian J. Davis
(74) Attorney, Agent, or Firm—Akin Gump Strauss Hauer & Feld, LLP

(57) ABSTRACT

The invention concerns a novel method for industrial preparation of disodium 2,2'-dithiobis(alkylsulphonates), and in particular disodium 2,2'-dithiobis(ethanesulphate) (dimesna). Said novel method is summarized by the reaction diagram (A). In diagram (A), Hal represents a halogen atom, and preferably a bromine atom; M represents a sodium or potassium atom; and n represents an integer ranging between 0 and 2.

10 Claims, No Drawings

METHOD FOR PREPARING DISODIUM 2,2'-DITHIOBIS(ETHANESULPHONATE)

This application is a 371 of PCT/FR01/02312 filed Jul. 17, 2001.

The present invention describes a novel process of industrial preparation of disodium 2,2'-dithiobis(alkylsulfonates), and in particular the preparation of disodium 2,2'-dithiobis (ethanesulfonate) (dimesna).

Dimesna (as well as its monomer, mesna) is a therapeutic agent useful in particular as a chemoprotectant for certain types of cancers by reducing the toxic effect of Platinum complexes commonly used in chemotherapy (like cisplatin). Of relevance is Patent PCT Application WO 98/14426.

A certain number of patent applications are relevant to the processes of preparation of dimesna or mesna. Among them, one can note the PCT application WO 98/14426. The processes related to the preparation of dimesna or homologous products can be summarized in the following scheme. Hal represents a halogen atom and R2 represents a radical SO3M or PO3M2, while M represents sodium, potassium or hydrogen. In the generic formula (IIb) R2 represents exclusively the radical PO3M2:

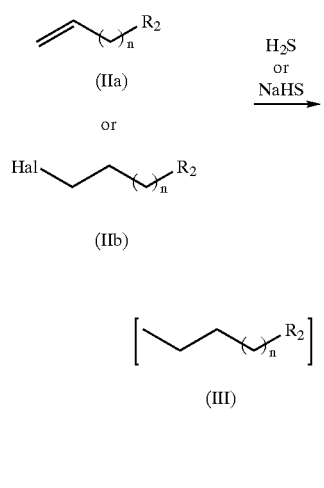

In this process, intermediate (III) is not isolated. It is directly transformed by heating in the presence of oxygen to disulfide (Ia).

Another way of preparing symmetric disulfides such as dimesna is described in *Phosphorus, Sulfur and Silicon* 1994, 95–96, 351–352. This method can be summarized by the following synthetic scheme in which (BTS)2 represents the disulfide of 2-mercaptobenzotriazole:

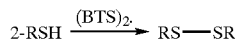

A common problem in the synthesis of mesna or dimesna resides in the presence of many impurities in the desired product. These impurities are usually salts like sodium bromide or acetates generated by the current synthetic processes. The necessary removal of such impurities represents an important waste of time and money.

The present invention describes a novel process which allows the synthesis of disodium 2,2'-dithiobis (alkylsulfonates), and in particular the synthesis of mesna, without the common impurities resulting from the previous processes.

This novel process of industrial synthesis of disodium 2,2'-dithiobis(alkylsulfonates) is summarized in the following scheme:

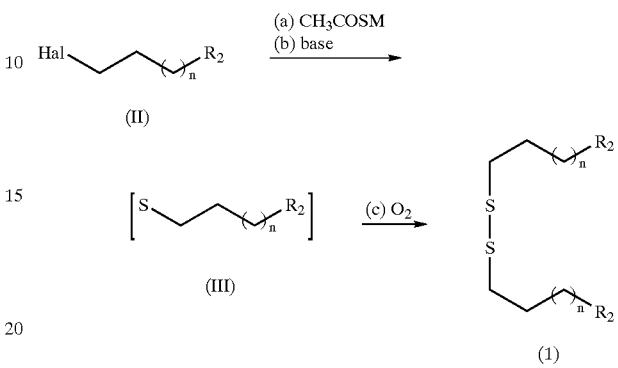

In the previous scheme, Hal represents a halogen atom, in particular a bromine atom, M represents sodium or potassium atom while n represents an integer from 0 to 2. Steps (a) and (c) are preferentially carried out by heating. M represents preferentially sodium.

This invention is therefore about the industrial preparation process of a disulfide of general formula (I)

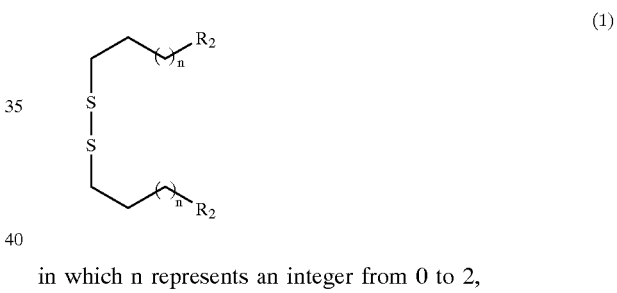

in which n represents an integer from 0 to 2, with the following steps:

(a) treatment of a compound of general formula (II)

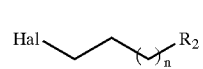

in which Hal represents a halogen atom, with a thiolacetate of general formula CH3COSM in which M represents sodium or potassium;

(b) reaction of the resulting thiolacetate from step (a) with a base followed by acid neutralization; and (c) reaction of the resulting intermediate sodium mercaptoalkylsulfonate of general formula (III)

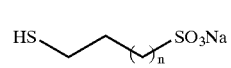

with oxygen to yield the disulfide of general formula (I);

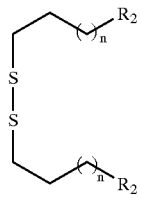

(1)

(d) ethanol addition to the resulting reaction mixture from (c), heating to obtain a clear solution, cooling and washing (at least once) of the resulting solid with ethanol.

In this process, sodium thiolacetate CH3COSNa from step (a) can be obtained by reacting thiolacetic acid with a base containing the metallic counterion M, for instance NaOH or KOH when M represents sodium or potassium. Preferentially, M represents sodium, while step (a) is carried out by heating at a temperature superior to ambient temperature, for instance at a temperature between 25 and 100 degree Celsius, particularly between 75 and 85 degree Celsius.

The base necessary to hydrolyze the thiolacetate intermediate in step (b) is preferentially NaOH or KOH. Due to the exothermic character of the reaction, the reaction mixture resulting from step (a) is preferentially cooled to a temperature closer or inferior to ambient temperature (for instance if the preferred temperature for step (a) is between 75 and 85° C., step (b) is preferentially carried out with an initial temperature between 45 and 55° C., or even at a temperature between 0 and 45° C.). After this step, the pH of the reaction mixture should be between 6 and 8, preferentially between 6.5 and 7.5 and more preferentially between 7 and 7.2. The acid used in this neutralization is preferentially acetic acid, although any other suitable acid can be employed.

In step (c), the reaction mixture is preferentially heated at a temperature superior to ambient temperature, for instance at a temperature between 30 and 90° C., preferentially between 50 and 60° C. Oxygen is bubbled in the reaction mixture at a pressure between 0 and 5 bars, preferentially at atmospheric pressure. Alternately, hydrogen peroxide in approximate stoichiometric amounts can be used in place of gaseous oxygen. Reaction times are in the range of 2 to 10 hours and more, for instance 8 hours (the actual reaction time can be monitored by HPLC, TLC or any other appropriate means). After step (c), the reaction mixture may be filtered, for instance on holes between 0.5 and 5 μm, preferentially between 0.5 and 1 μm.

In step (d), the volume of added ethanol is a function of the reaction mixture volume V obtained after step (c) and is preferentially between 0.8 and 1.2 times V, more preferentially between 0.9 and 1.1 times V. The resulting mixture after ethanol addition is heated at a temperature high enough to obtain a homogeneous solution, for instance between 60 and 70° C. The cooling of this resulting solution is usually carried out slowly, preferentially by letting the solution stand for several hours at room temperature and subsequently cooling it and maintaining it for at least 30 min between 0 and 40° C., more preferentially between 0 and 10° C. The first washing is preferentially carried out with a mixture of ethanol/water of typical ratio of at least two volumes of ethanol for 1 volume of water, for instance three volumes of ethanol for 1 volume of water.

After step (d) the resulting product can be dried in a ventilated oven. The absence of residual ethanol/water can be monitored by NMR. Alternately, this product may be dried by any other suitable methods.

This process applies to the preparation of compound (I) where n is preferentially 0, (I) being therefore dimesna.

Unless explicitly defined, all the technical and scientific terms used in this invention have their signification similar to the one commonly understood by an ordinary specialist of the field. All the cited publications, patent applications and patents are mentioned for the sole purpose of references.

The following example illustrates the described procedures and shall not be considered as a limitation of the present invention.

EXAMPLE

Preparation of disodium 2,2'-dithiobis(ethanesulfonate) (dimesna)

In the following procedure the term "around" applied to a temperature corresponds to an interval of ±5° C. around the indicated temperature.

In a first reactor R is prepared a soda solution by mixing 2 L of demineralized water and 0.65 Kg of soda (1.03 equivalents). The obtained solution is made homogeneous at around 5° C. 0.388 Kg of thioacetic acid (1.08 eq) are then added to this solution while maintaining the temperature to around 5° C. 0.1 L of demineralized water is used to rinse the addition funnel containing thioacetic acid and is also added to the reaction mixture. Reactor R is then heated at around 20° C. and stirred at this temperature for 30 min.

In a second reactor R' is placed 1 Kg of sodium bromoethanesulfonate (1.16 eq). To this reactor is added the content of reactor R. Reactor R is rinsed with 0.1 L of demineralized water and the resulting rinsing water is added to reactor R'. Reactor R' is heated to around 80° C. and stirred at this temperature for around 1 h30. The end of the reaction is monitored by HPLC. The solution is then cooled at around 50° C.

In another reactor is prepared a soda solution by mixing 2 L of demineralized water and 1.36 Kg of soda. The obtained solution is made homogeneous at around 20° C. This resulting solution is added in reactor R' yielding an exothermic reaction. The resulting reaction mixture is stirred for around 30 min. . The end of the reaction is monitored by HPLC. The solution is then brought to around 55° C.

In another different reactor, a solution of acetic acid is prepared by mixing 0.3 L of demineralized water and 0.3 L of acetic acid. This solution is added to reactor R'. Once pH is controlled to be in the range of 7.0–7.2 oxygen is bubbled into the reaction mixture while the temperature of the obtained mixture is maintained at around 55° C. After 8 h of bubbling, pH is checked again and the end of the reaction is monitored by HPLC (if conversion is not complete, oxygen bubbling is continued at a temperature of around 55° C. as long as needed). The reaction mixture is then filtrated on a filter of 1 μm diameter holes.

Ethanol is then added to the filtrated mixture in equal volume and the resulting mixture is thoroughly stirred. Precipitates are eventually forming, which are dissolved by heating at around 65° C. The mixture is then progressively cooled to around 20° C. and may be left standing overnight at this temperature. The resulting mixture is then cooled down to around 5° C. and maintained at this temperature for 1 h. The suspension is then filtrated.

In another reactor is prepared an ethanolic solution by mixing 0.1875 L of demineralized water and 0.5625 L of ethanol. This solution made homogeneous at 20° C. is used to wash the resulting "cake" obtained from the previous suspension. The "cake" is washed another time with 0.75 L of ethanol and the solid is dried in a ventilated oven at 60°

C. until NMR displays no more ethanol. 0.70 Kg of dimesna are then obtained.

What is claimed is:

1. A process for the industrial preparation of a disulfide of formula (I)

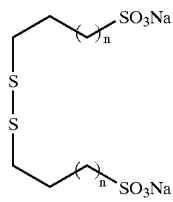

in which n represents an integer between 0 and 2, said process comprising the following steps:

(a) providing a solution containing a compound of formula (II)

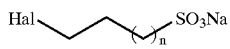

in which Hal represents a halogen atom, and reacting the formula II compound with a thioacetate of the formula $CH_3C(O)SM$ in which M represents sodium or potassium to form a thioacetate alkane sulfonate intermediate;

(b) reacting the thioacetate intermediate from step (a) with a base to remove the acetate moiety and form a sodium mercaptoalkanesulfonate intermediate of formula III

(c) adjusting the pH of the solution by adding an acid;

(d) reacting the intermediate sodium mercaptoalkanesulfoflate of formula III with oxygen to yield the formula (I) disulfide; and (e) adding ethanol to the formula I disulfide obtained in step (d), followed by heating to dissolve the precipitates, then cooling and washing the resulting solid with ethanol.

2. Process according to claim 1, in which M represents sodium in step (a).

3. Process according to claim 1 or 2, in which the base in step (b) is sodium hydroxide.

4. Process according to claim 3, in which the volume of ethanol added during step (e) is in between 0.8 and 1.2 times the volume of the reaction mixture obtained at step (d).

5. Process according to claim 4, in which the volume of ethanol added during step (e) is in between 0.9 and 1.1 times the volume of the reaction mixture obtained at step (d).

6. Process according to claim 1, in which the washing of step (e) includes a first step of washing with a mixture of ethanol/water, with a ratio of 2 volumes of ethanol per volume of water.

7. Process according to claim 1, in which the washing of step (e) includes a first step of washing with a mixture of ethanol/water, with a ratio of 3 volumes of ethanol per volume of water.

8. Process according to claim 1, in which step (d) is followed by a filtration of the reaction mixture on a filter of hole sizes comprised between 0.5 and 5 μm, which is carried out just before step (e).

9. Process according to claim 8, in which the filter has hole sizes comprised between 0.5 and 1 μm.

10. Process according to claim 1, in which n=0.

* * * * *